United States Patent [19]
Brenneman

[11] Patent Number: 5,957,929
[45] Date of Patent: Sep. 28, 1999

[54] EXPANDABLE STENT APPARATUS AND METHOD

[75] Inventor: Rodney A. Brenneman, San Juan Capistrano, Calif.

[73] Assignee: Micro Therapeutics, Inc., Irvine, Calif.

[21] Appl. No.: 08/850,320

[22] Filed: May 2, 1997

[51] Int. Cl.[6] .................................................. A61F 11/00
[52] U.S. Cl. ............................................... 606/108; 606/1
[58] Field of Search ................................... 606/108, 194, 606/195, 191, 192, 198; 623/1, 11, 12

[56] References Cited

U.S. PATENT DOCUMENTS

| 5,147,387 | 9/1992 | Jansen et al. | 623/1 |
| 5,226,913 | 7/1993 | Pinchuk | 623/1 |
| 5,306,294 | 4/1994 | Winston et al. | 623/1 |
| 5,405,379 | 4/1995 | Lane | 623/1 |
| 5,540,713 | 7/1996 | Schnepp-Pesch et al. | 606/198 |
| 5,653,696 | 8/1997 | Shiber | 604/267 |

*Primary Examiner*—Michael Buiz
*Assistant Examiner*—Vy Quang Bui
*Attorney, Agent, or Firm*—Crockett & Fish; K. David Crockett, Esq.

[57] ABSTRACT

An expandable stent has a sheeted material which is expanded from a compacted configuration to an expanded configuration. The sheet is maintained in the compacted configuration at least in part by operation of a dynamic force, and the expansion occurs at least in part by removal of the dynamic force. In preferred embodiments, a biocompatible sheeted material is wrapped around a retaining wire to produce a compacted configuration, and the retaining wire is rotated to maintain the compacted configuration during insertion of the stent into a patient. The rotation is continued while the stent is positioned, and then the rotation is stopped or slowed to permit expansion of the sheet.

19 Claims, 5 Drawing Sheets

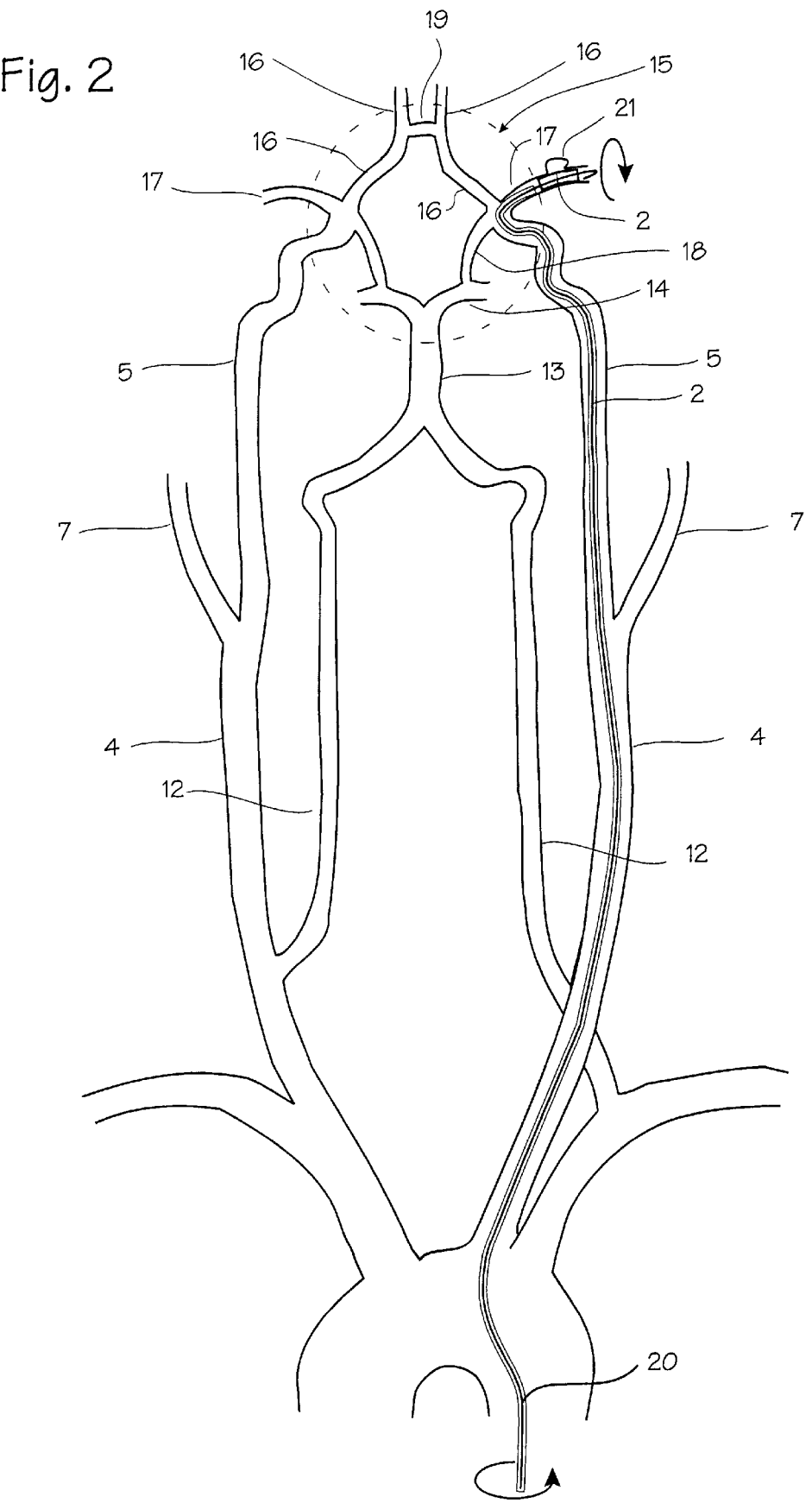

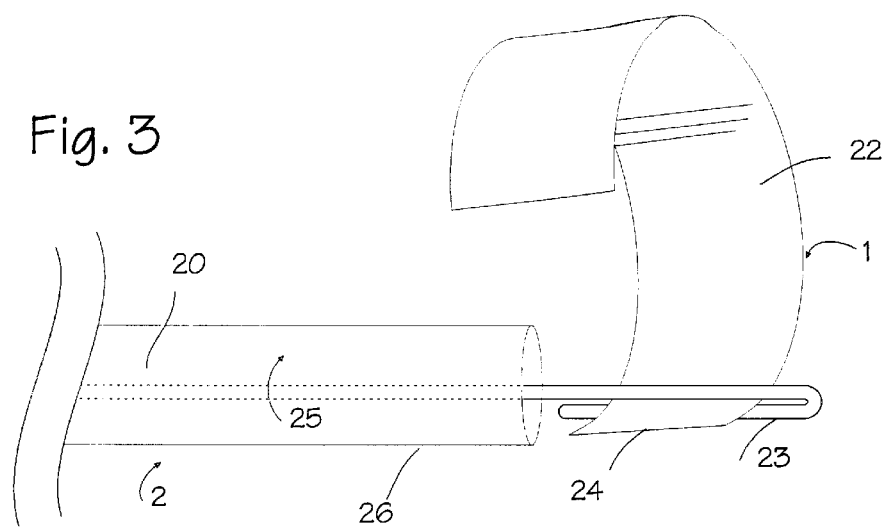
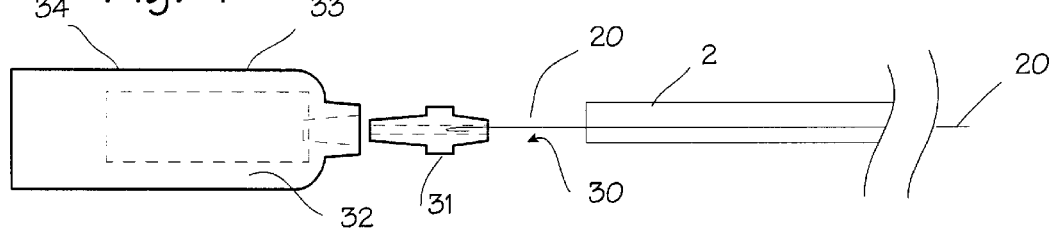
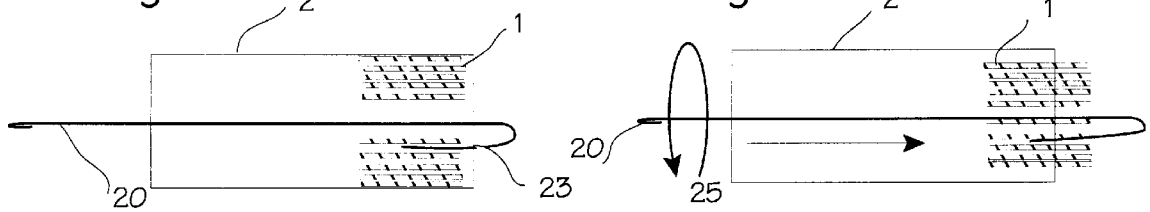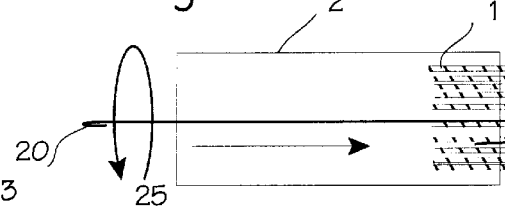
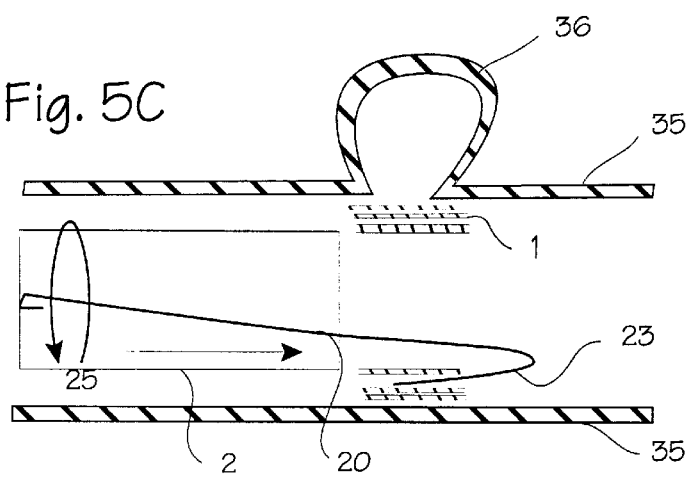

EXPANDABLE STENT APPARATUS AND METHOD

FIELD OF THE INVENTION

This invention relates to expandable stents.

BACKGROUND OF THE INVENTION

Stents are endoprostheses which can be deployed into the lumen of an artery or vein, a common bile duct, the urethra or other body passageway. Stents may be employed in such passageways for many purposes, including expansion of a lumen, maintenance of the lumen after expansion, and repair of a damaged intima or wall surrounding a lumen. With respect to arteries, for example, stents may be used as, or in conjunction with, intralumenal grafts in the maintenance of patency of a lumen following angioplasty. In such cases a stent may be used to prevent restenosis of the dilated vessel, to prevent elastic recoil of the vessel, or to eliminate the danger of occlusion caused by "flaps" resulting from intimal tears associated with the angioplasty. In other instances, stents may be used to treat aneurysm, tears, dissections and other continuity faults, as, for example, in the splenic, carotid, iliac and popliteal vessels. By way of further example, it is known to use a stent to maintain the patency of a urethra compressed by an enlarged prostate gland.

In one class of expandable stents commonly referred to as "rolled" stents, a sheeted material is rolled onto the outer distal circumference of a support member or "core". The sheeted material is then positioned at a targeted treatment area and expanded. Rolled stents can be characterized according to: (1) the method by which the rolled sheet is maintained in a compressed configuration; and (2) the method by which the sheet is expanded.

Lane, Self Expanding Vascular Endoprosthesis for Aneurysms, U.S. Pat. No. 5,405,379 (Apr. 11, 1995) describes a stent which employs a self expanding sheet. The sheet is forcibly rolled into a compressed configuration, and then inserted into a catheter to maintain the compressed configuration. Expansion takes place by ejecting the sheet from the end of the catheter.

Kreamer, Intraluminal Graft, U.S. Pat. No. 4,740,207 (Apr. 26, 1988) describes a rolled stent in which a sheet of stainless steel is rolled around an angioplasty type balloon. After being introduced into a treatment area, the sheet is expanded by inflating the balloon with a fluid. In this case compression is maintained during the early stages of deployment by the relaxed nature of the sheet in the compressed configuration, i.e., the internal mechanical resistance of the sheet to deformation. Expansion of the sheet, on the other hand, occurs under radial pressure exerted by the expanding balloon.

Sigwart, Intravascular Stent, U.S. Pat. No. 5,443,500 (Aug. 22, 1995) describes a stent in which a flat sheet is perforated to form a reticulated or lattice type structure having a racheting locking mechanism. Compression in stents according to the Sigwart patent are maintained by a holding wire or adhesive, and the sheet is contemplated to be expanded under the influence of an angioplastyballoon.

Sigwart also describes another stent comprising an elastic stainless steel mesh. The diameter of the mesh is slightly larger than the normal inner diameter of the vessel to be treated, so that the mesh can exert a residual radial pressure on the arterial wall after being implanted. Before being introduced into a patient's blood vessel the stent is reduced in diameter. The reduced diameter is maintained while advancing the stent into a target treatment area by an outer sleeve. Once the device is implanted, the stent is deployed by withdrawal of the outer sleeve. In this instance, compression is thus maintained by the outer sleeve, and expansion is achieved by removal of the outer sleeve.

Alfidi and Cross, Vessel Implantable Appliance and Method of Implanting It, U.S. Pat. No. 3,868,956 (Mar. 4, 1975) describes a stent which utilizes a recovery alloy such as nitinol. In such stents an initial expanded configuration is permanently set into the alloy by heating the material to a relatively high temperature while the alloy is maintained in the expanded configuration. The alloy is then cooled and deformed to a compressed configuration. The compressed configuration is retained at room temperature, but recovers to the expanded configuration when reheated to a transition temperature. Here, compression is maintained during the early stages of deployment by the internal mechanical resistance of the alloy against deformation, and the sheet is expanded under the influence of heat.

These and all other known teachings reflect the accepted wisdom that rolled stents are to be maintained in their compressed configurations by the operation of static forces (e.g., biasing produced by the internal mechanical resistance of the sheet to deformation, presence of holding wires, outer sleeves and so forth), while expansion of the sheeted materials is to be produced by application of a dynamic force (e.g., radial pressure exerted by an expanding balloon, application of heat, removal of a holding wire or sheath, and so forth). While such strategies undoubtedly have their benefits, it is useful to have stents which operate outside of these accepted constraints.

Where the stent is to be deployed in very small vessels of the body, such as the arteries in the brain, the size of the stents is quite small, and the material used for the stents is on the order of 0.0001–0.0004 inches thick. The small size and extreme thinness of the stent material makes it difficult to deploy the stent using the typical push-pull type deployment mechanisms generally used for stents. The frictional force exerted on the stent by the catheter sheaths and cores as they slide over the stent often tears the stent. In our co-pending U.S. patent application Ser. No. 08/762,110, filed Dec. 9, 1996, we provide a number of devices that do not require any sliding movement of the stent or catheter sheath relative to each other. The devices described below provide additional mechanisms and methods for deploying stents while minimizing the frictional forces operating between the stents and the catheters used for their insertion.

SUMMARY OF THE INVENTION

Stents for intra-cranial use and methods for using these stents are described in detail below. The physical characteristics of prior art balloon expandable stents and self expanding stents make them clearly unsuitable for intra-cranial use, because of their delivery profile, their lack of flexibility and their tendency to temporarily occlude the vessel during deployment. They have not been proposed for intra-cranial use. Palmaz stents, Palmaz-Schatz™ stents, Wallstents, Cragg stents, Strecker stents and Gianturco stents and other stents are too rigid to allow placement in the cerebral blood vessels, some require a balloon for deployment, and all are too open to occlude or prevent blood flow into an aneurysm. Presented below are several embodiments of stents suitable for intra-cranial use, along with methods for using these stents to treat intra-cranial vascular disease.

The self expanding rolled sheet stent is suitable for use in the intra-cranial arteries. The rolled sheet is made of Elgiloy™, nitinol, stainless steel, plastic or other suitable material, and is imparted with resilience to urge outward expansion of the roll to bring the rolled stent into contact with the inner wall of a diseased artery. The rolled sheet is adapted for easy insertion and non-deforming radial flexibility to facilitate tracking along the tortuous insertion pathways into the brain. In some embodiments, as much of the material of the stent is removed as is consistent with eventual creation of a solid walled stent upon unrolling of the stent within the blood vessel. The unrolled stent may be two or more layers of Elgiloy™, thus providing radial strength for the stent and creating at least a slight compliance mismatch between the stent and the blood vessel, thereby creating a seal between the stent and the blood vessel wall. For placement, the stent is tightly rolled upon or captured within the distal tip of an insertion catheter. The release mechanism is extremely low profile (3 Fr or less), and permits holding the rolled stent in a tight roll during insertion and permits atraumatic release when in the proximity of the site of arterial disease, without completely occluding the vessel with the deployment catheter. The stent can be placed in the intra-cranial blood vessels (arteries and veins) of a patient to accomplish immediate and complete isolation of an aneurysm and side branches from the circulatory system. The stent can be placed so as to partially occlude or modify blood flow into an aneurysm. The stent can be placed so as to allow for injection of coils (GDC coils or Gianturco coils) or embolic material into an aneurysm and prevent wash-out of the coils or embolic material. The stent may be placed across a target site such as an aneurysm neck, origin of a fistula, or branch blood vessels feeding a tumor in order to redirect the flow of blood away from the target. It can be used as a stand alone device which is left in the intra-cranial artery permanently, or it may be used as a temporary device which allows for immediate stabilization of a patient undergoing rupture of a blood vessel an aneurysm or awaiting open skull surgery for clipping or resection of an aneurysm. The stent can be used for stabilization and isolation of a vascular defect during surgery of the vascular defect. Another advantage of this type of stent is that it can be wound down should repositioning be required prior to full release. It is possible to rewind and reposition or remove the device using a crooked rotating wire or other grasping tools.

The present invention is directed to expandable stents having a sheeted material configurable in both a compacted configuration and an expanded configuration, in which the compacted configuration during deployment is maintained at least in part by operation of a dynamic force, and expansion to the expanded configuration occurs at least in part by removal of the dynamic force.

In preferred embodiments, a biocompatible sheeted material is wrapped around a retaining wire to produce the compacted configuration, and the retaining wire is rotated to maintain the compacted configuration during insertion of the stent into a patient. The rotation is continued while the stent positioned, and then the rotation is stopped or slowed to permit expansion of the sheet. Counter rotation may be used to enhance expansion, if desired.

BRIEF DESCRIPTION OF THE DRAWINGS

FIG. 2 is schematic diagram of the vascular of the brain illustrating the circle of Willis and arteries supplying the circle of Willis.

FIG. 3 is a diagrammatic representation of a stent according to the present invention.

FIG. 4 is a diagrammatic representation of a motor drive used for the stent and its connection to the system.

FIGS. 5a, 5b and 5c are a diagrammatic representations of a the stent in the process of deployment.

DETAILED DESCRIPTION OF THE DRAWINGS

Figure 1:
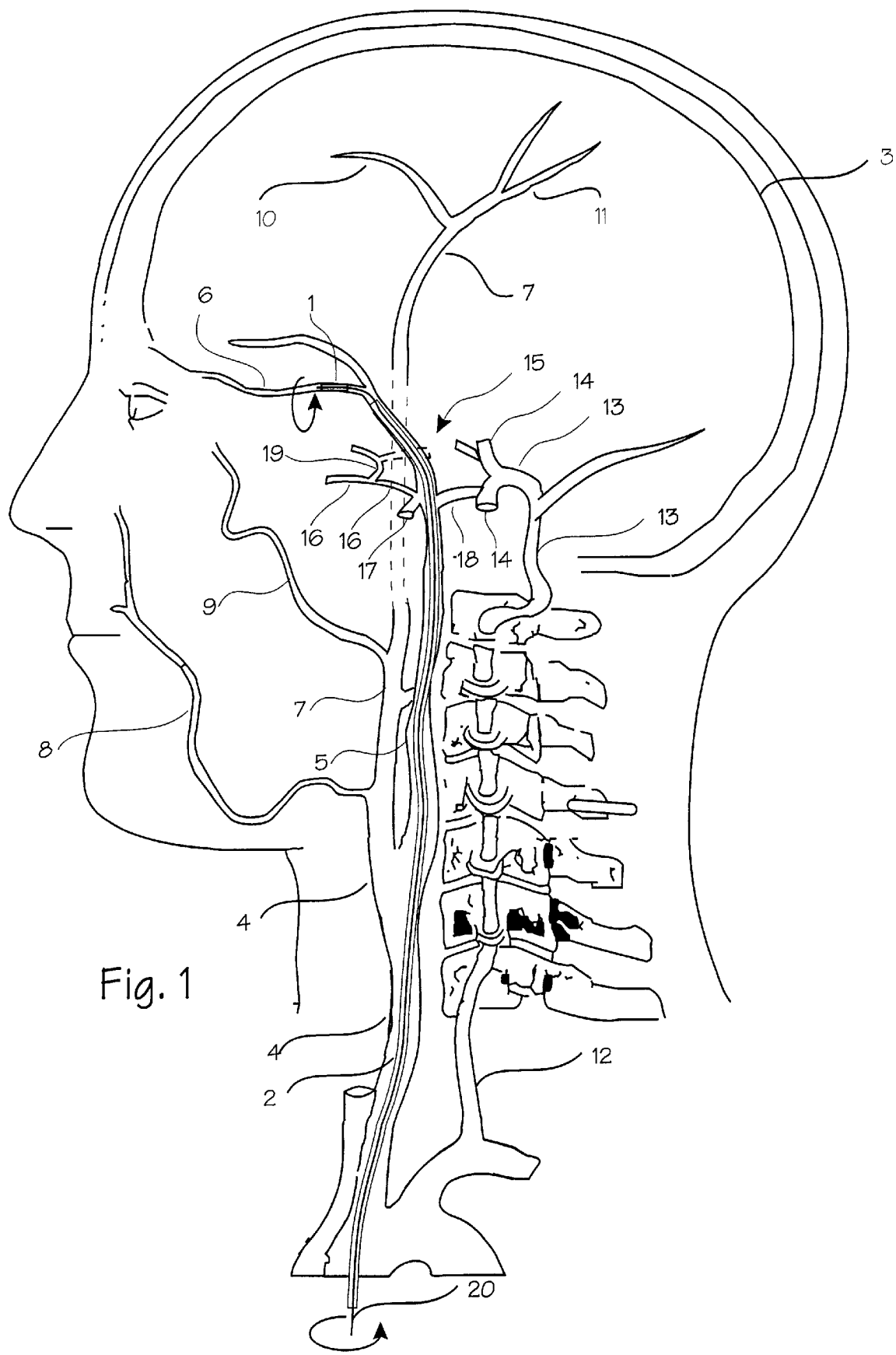
FIG. 1 is a schematic diagram of the vasculature of the brain showing a typical placement of an intra-cranial stent.

The stent delivery system is particularly well suited for delivery of stents into very small vessels in the body, such as the blood vessels within the brain. FIGS. 1 and 2 show the vasculature of the brain in sufficient detail to understand the invention. The brain 3 is supplied with blood through the carotid and the vertebral arteries on each side of the neck. The important arteries include the common carotid artery 4 in the neck, which will be the most common access pathway for the stent, the internal carotid 5 which supplies the opthalmic artery 6. The external carotid 7 supplies the maxillary artery 8, the middle meningeal artery 9, and the superficial temporal arteries 10 (frontal) and 11 (parietal). The vertebral artery 12 supplies the basilar artery 13 and the cerebral arteries including the posterior cerebral artery 14 and the circle of Willis indicated generally at 15. Also supplied by the internal carotid artery are the anterior cerebral artery 16 and the middle cerebral artery 17, as well as the circle of Willis, including the posterior communicating artery 18 and the anterior communicating artery 19. These arteries typically have an internal diameter of about 1 mm to 5 mm, most commonly from 2–4 mm. The methods and devices described herein allow access to these arteries and placement of a stent in these arteries. In FIG. 1, the insertion catheter 2 and stent 1 are shown in an exemplary use, threaded through the common carotid artery 4 and the internal carotid artery 5, with the stent extending into the anterior cerebral artery 16. The rotating wire 20 extends from the proximal end of the insertion catheter 2 to the distal end, and into the stent to impart rotation to the stent.

FIG. 2 shows the same blood vessels in a schematic view that better illustrates the circle of Willis and the arteries which supply this important anatomic feature. The circle of Willis 15 is a ring of arteries connecting the internal carotid arteries and the basilar artery (and hence the left and right vertebral arteries) to the anterior cerebral arteries 16, middle cerebral arteries 17 and posterior cerebral arteries 14. The system provides a redundant supply of blood to the cerebral arteries. Aneurysms, fistulas, AVM's and tumors occurring inside the brain, in the intracranial portion of the carotid arteries, vertebral arteries and basilar artery, in the circle of Willis or even deeper within the brain may be treated with the stents and delivery systems described below. FIG. 2 shows an exemplary use in which a delivery catheter 2 is inserted through the aorta into the common carotid, internal carotid and through the circle of Willis 15 into the middle cerebral artery 17 to treat an aneurysm 21 with a stent which is deployed while being rotated by rotating wire 20, as explained below.

In FIG. 3, the structure of the stent and stent delivery system are shown in detail. The stent 1 used with the system generally comprises a rolled sheet 22. The rolled sheet is sized appropriately to both fit within a delivery sheath when rolled tightly, and fit snugly within a blood vessel when released and allowed to open to a loosely rolled configuration. The sheet 22 is releasably coupled to the insertion catheter 2 via the retaining wire 20 which has a tightly bent crook 23 which grasps the inner edge 24 of the stent. The retaining wire 20 is rotated in the direction of arrow 25 such that the sheet 22 tends to wrap around the retaining wire 20. Rotation in this manner tends to cause the sheet 22 to assume an at least partially compacted configuration. The sheet is 22 initially wrapped around the retaining wire and slipped into the distal end 26 of the insertion catheter. Once compacted in this manner, the stent 1 can be introduced into the insertion catheter 2 for deployment into an artery or other passageway. When inserted into the insertion catheter 2, the retaining wire securely holds the stent in the tight roll within the insertion catheter.

The proximal end of the stent delivery system is shown in FIG. 4. The retaining wire 20 is attached at its proximal end 30 to a proximal hub 31 and an electric motor 32 which is housed within the handle 33. The motor 32 is used to rotate the retaining wire 20 and the stent 1. The motor may be operated to rotate the retaining wire 20 and the stent 1 in the direction which urges sheet to tighten upon itself and remain in a small diameter configuration (indicated by arrow 25). The motor is controlled with a spring loaded thumb slide 34. A portion of the stent 1 passes through a catheter 2, but during at least a portion of its travel during deployment in a target lumen, the sheet is maintained in a compacted configuration at least partially as a result of continued rotation of the stent 1 by the motor 32.

The motor 32 is presently contemplated to have an operational range of between zero and 200 revolutions per minute (rpm). It is considered advantageous for the motor 32 to include a variable speed control, and the motor may have a reverse mode. The motor may be battery operated to avoid the need for a power cord. It is also desirable to have a manual turning device, such as the proximal hub 31 which is connected directly to the retaining wire 20, or to the motor 32, or indirectly coupled to the retaining wire 20 through a clutch mechanism. For small rotations needed for some manipulations of the stent during and after placement, it is sufficient to rotate the entire handle and motor assembly by hand. A typical retaining wire comprises a wire 100–175 cm long, and may measure about 0.005 to 0.020 inches (5–20 mils, or 0.1–0.4 mm) in diameter. Of that length, about 0.5 cm at the distal end is bent around to form the retaining wire crook. The proximal end is attached to the proximal hub connector in motor and handle assembly. The retaining wire may be releasably attached with connections such as the couplings typically used for rotational atherectomy catheters and intravascular ultrasound catheters. Preferred materials for the retaining wire include stainless steel and nitinol.

Turning in greater detail to specific elements of the stent 1, it should be apparent that the sheet 22 can have any suitable composition, surface characteristics, shape, thickness, elasticity and so forth. When used in the illustrated use for blocking off side wall aneurysms or side vessels in an artery, the stent sheet material is preferably made of Elgiloy or nitinol (with nickel-rich nitinol being preferred). The sheets preferably comprise biocompatible material, but there may be circumstances in which stent is to be used for occlusion or tissue disruption, in which case a non- or only minimally compatible material may be preferred. Biocompatible materials include various metals, synthetics and ceramics, and may also include living tissue or a composite of living tissues and non-living material such as described in Turi, Composite Intraluminal Graft, U.S. Pat. No. 5,556,414 (Sep. 17, 1996). Thus, the terms "sheet" and "sheeted material" are used herein in a very broad sense, including relatively thin meshes and other materials having a relatively large flattened surface.

Sheets according to the present invention may advantageously have a smooth outer surface to minimize trauma to tissues with which the sheet comes in contact. The surface may also include an anti-restenosis coating such as heparin, fibrin or a fibrin/elastic compound. Other useful coatings, such as a degradable mucin or other coating to minimize friction, may also be used. The stent may be treated so as to be radioactive, in order to minimize hyperplasia and excessive neointimal growth. A radiographically opaque coatings, such as tin or platinum, have proven to enhance radiographic visibility of the stent during and after deployment. Tantalum plating of about 1000 to 10,000 Å thickness is sufficient to provide good visibility of the stent when rolled in many layers within the insertion catheter, and a plating of 500 to 5000 Å on both sides of the sheet is sufficient for good visibility of the stent when expanded into just a few layers within the blood vessel.

As with the other characteristics mentioned herein, there are numerous contemplated variations for the shape and thickness of the sheet. The sheet should have sufficient size and stiffness to handle the relatively high stresses involved. Thus, the length of the sheet employed to treat aneurysms of the carotid arteries in an adult male may advantageously measure about 2.5 mm in longitudinal length 1 and about 40 mm in wrap length w. For aneurysms of the cavernous carotid arteries, the stent may be telescoped to cover distances as much as 10 mm or more. Where the stent is deployed in smaller vessels, however, such as the cerebral arteries, the corresponding dimensions may be 1 mm in length and 20 mm in wrap length. The thickness may measure 0.0001" to 0.0004" (0.1–0.4 mil, or 0.0025–0.01 mm) when the sheet is made of Elgiloy. The thickness of 0.0002–0.0003"" (0.2–0.3 mil, or 0.0050–0.0075 mm) has worked best in bench tests and animal studies, resulting in negligible crimping from the crook and providing for easy deployment without the tearing associated with push-type deployment methods. Nitinol sheets may be slightly thicker and may allow for greater radial force applied by the stent against the blood vessel wall. The wrap length of the stent may vary according to the size of the target vessel and the number of overlapping layers desired in the deployed configuration.

The stent sheets may be perforated to any degree necessary to encourage tissue ingrowth or to allow for some blood flow through the stent wall. Although the sheets illustrated are rectangular or ribbon shaped, the sheets used for the stents need not be rectangular. A triangular shape, for example, may also be feasible, with either an edge or a point of the triangle being grasped by the retaining wire. The wrap length of the sheet may be variable, and may be long enough to wrap the sheet around itself three, four, five or more times, or it may be short enough so that the wrap length is substantially equal to the circumference of the target vessel, in which case the sheet will have a single layer after deployment. In such cases, it may be desirable to translate the retaining wire within the lumen back and forth during deployment to reduce the possibility of gaps. The stent may be telescoped to allow for greater length than its straight rolled configuration would otherwise allow. Also, the rotational method of deployment may be used with the extreme cases of a wire coil stent wherein the stent comprised a coil of round or square wire (as opposed to the ribbon shape used in the illustrations).

The use of Elgiloy™ or nitinol provides elasticity that is suitable for easy deployment of the stent, providing for adequate self expandability and also providing adequate strength for the stent after deployment. The crimping at the inner edge of the stent, where the crook grasps the sheet, is negligible or acceptably small with Elgiloy and nitinol. Other materials may be used which provide relatively more or less of a self expanding quality. One alternative is to make the sheet with material that has high elasticity, and will expand to a substantially predetermined shape upon cessation of rotation. In other instances, the sheet may have little or no elasticity, and may be optimally deployed by ceasing rotation, and then unwinding the sheet by rotation in the opposite direction, by balloon expansion, or otherwise applying active force upon the sheet. There may also be greater elasticity in one dimension than in another Lumenal deployment occurs by rotating the stent 1 while extending it from the open distal end of the catheter. While still under the influence of continued rotation, the stent 10 is pushed from the distal end of the insertion catheter, using the motor and handle assembly. The stent is navigated through any length of blood vessel while rotating, and fed to a target area for deployment, where the rotation is stopped or even reversed slightly to unwrap the sheet 22. Simple manual rotation of the retaining wire may be used to assist in proper deployment. The stent 1 is then pushed, pulled, or otherwise manipulated to free the retaining wire 20 from the sheet, and the stent is withdrawn. FIGS. 5a, 5b and 5c illustrate the method of deployment of a stent which is enabled by the device. In FIG. 5a the stent 1 is positioned at the distal end of the insertion catheter 2. The stent is still wrapped around the retaining wire and secured by the crook of the wire. In FIG. 5b, the retaining wire 20 is rotated in the direction necessary to tighten the stent, and this rotation causes the stent to tighten into a tighter roll (the diameter may remain the same or become smaller, depending on the speed of rotation and the flexibility of the stent) and also causes the stent to rotate with the retaining wire. As illustrated in FIG. 5b the stent 1 is advanced out insertion catheter 2. The longitudinal movement of the stent within the insertion catheter is facilitated by the rotation, and the stent 1 is maintained in a tightened configuration by rotation of the retaining wire 20 in the direction of arrow 25. The stent also does not spread longitudinally during the rotation, and this also facilitates deployment (although the rolled sheet may be telescoped to spread it out and cover a length of the blood vessel). Finally, as shown 5c, the stent is pushed longitudinally out of the distal end of the insertion catheter and into the lumen of the blood vessel 35 in position to close off the aneurysm 36. The retaining wire may be used to push or pull the stent into better position as it is rotating. Rotation is ceased when the position is acceptable, whereupon the stent opens fully. Fully unwinding of the stent can be ensured by counter-rotating the retaining wire (with the motor in reverse, or by hand turning the handle or the proximal hub). To release the stent, the retaining wire is pushed distally until the crook slips off the stent. The retaining wire may again be used to push or pull the stent into better position, or adjust the inner layer to compact or spread the stent longitudinally. The crook may be used to re-engage the stent and resume rotation (in order to move or remove the stent) by advancing the retaining wire to a position distal of the stent and carefully slipping the crook between the layers and resuming rotation. With this technique, the stent may be used as a permanent stent or as a temporary stent, for blood vessels deep within the body, and in particular for blood vessels within the brain. When used as a permanent stent to occlude and aneurysm, the stent may constitute the primary treatment for the aneurysm. When used as a temporary stent, the stent may be placed to occlude an aneurysm before invasive surgery such as aneurysm clipping or ligation, thereby eliminating much of the risk inherent in open surgical techniques for treating aneurysms within the brain. After a successful clipping or ligation, the stent can be re-engaged and rotated, and pulled into the distal end of the insertion catheter. It should be apparent that, when used as a temporary stent in an interoperative setting, the retaining wire may be left in place and need not be removed from the stent at any time. The stent may also be used to control blood flow through the neck of an aneurysm in conjunction with coils, embolic materials or other devices, or it may operate as a primary treatment.

Figure 6A:
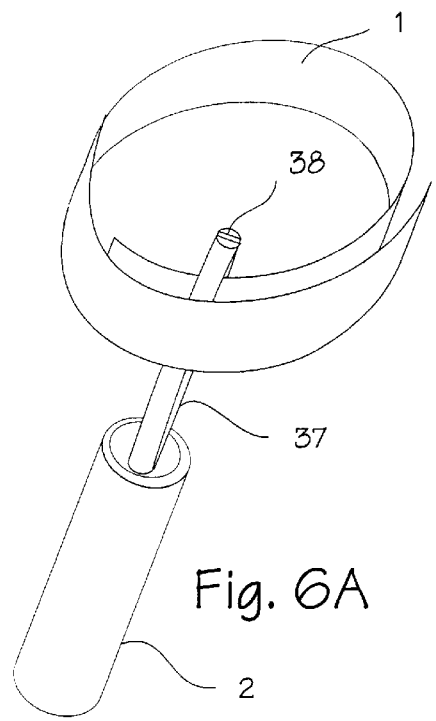
FIGS. 6A, 6B, 6C, 6D and 6E illustrate various methods of attaching and detaching a stent from the insertion catheter.
Figure 6B:
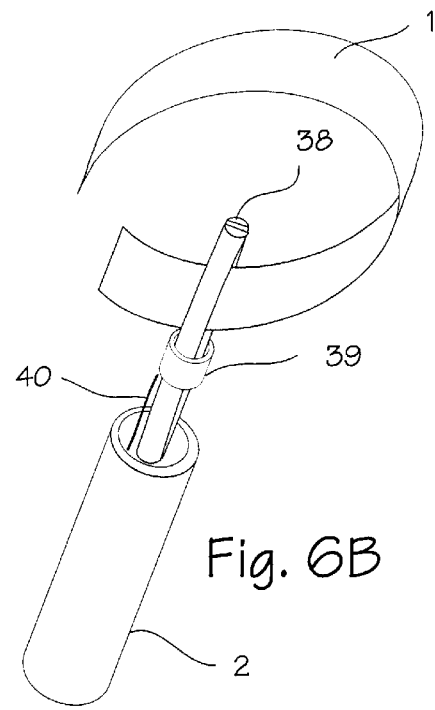
Figure 6C:
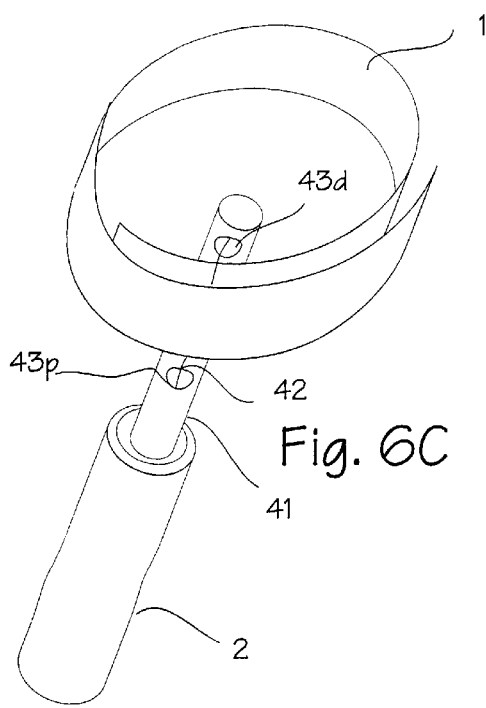
Figure 6D:
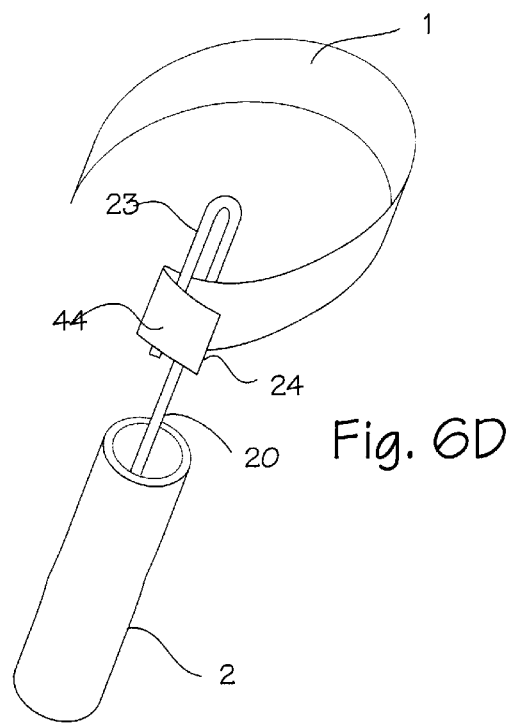
Figure 6E:
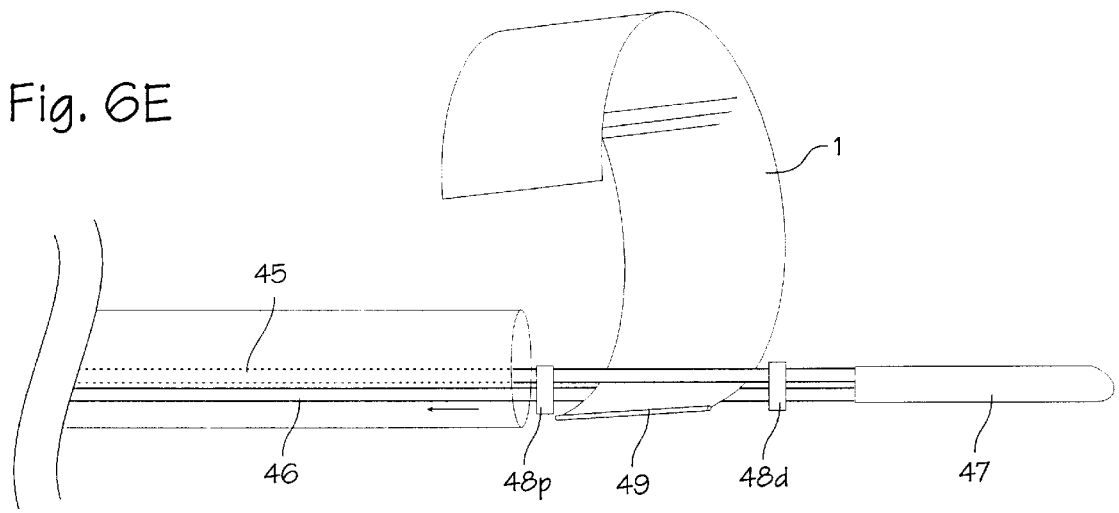

Other embodiments of distal rotatable and releasable connection may be used. As discussed above, the rotation of the stent is accomplished with the crooked retaining wire 20. Other stent rotation means are shown in FIGS. 6A through 6E. In FIG. 6A, the retaining means comprises a rotating shaft 37 with a split reed grasper 38 disposed on the distal end of the rotating shaft. The inside edge of the stent is trapped in the split reed, so that when the rotating shaft is spun from the distal end the stent is spun at the distal end. The stent is released when the split reed is pulled into the insertion catheter. FIG. 6B includes a compression ring 39 and pullwire 40 (which extends to the proximal end of the catheter) which can be used to compress the split reed during insertion and rotation, after which the compression ring can be pull proximally to allow the split reed to open slightly and release the stent. In FIG. 6C, the retaining means comprises a hollow shaft 41 (such as a hollow guidewire) combined with a pullwire retainer 42 runs generally through the center of the hollow shaft and but exits the center of the shaft though proximal wire port 43p, then runs over the inner edge of the stent before reentering the hollow shaft through distal wire port 43d. The stent is thereby trapped by the pullwire retainer 42. Rotation of the hollow shaft 41 causes rotation of the stent to tighten the stent configuration during insertion and longitudinal movement. When the stent is properly positioned, rotation is stopped and the pullwire retainer is pulled proximally to release the stent. FIG. 6D shows the crooked retaining wire 20, and the stent 1 which is trapped in the crook 23. The inner edge 24 of the stent is folded back, toward the outside surface, to form a flap 44. This outwardly facing flap provides extra holding power for the crook during rotation of the stent. FIG. 6E discloses yet another embodiment in which the stent 1 is retained between two spinning wires, a mounting spinning wire 45 and a retaining pullwire 46. Both wires extend to the proximal end of the insertion catheter 2 where they are attached to the proximal hub and motor. At the distal end, the mounting spinning wire is fixed to the guidewire tip 47, and the retaining pullwire is not fixed and therefore can be moved longitudinally in relation to the mounting spinning wire. The space between the wires is maintained tight by the rings 48d and 48p which are fixed to the mounting spinning wire, and through which the retaining pullwire 46 may move longitudinally. The stent will rotate with the wires, and release may be accomplished by pulling retaining pullwire 46 proximally away from the stent. The stent may be crimped, folded or provided with a beaded edge 49 on the inside edge 24 to ensure a good grip on the stent. Each of the embodiments can incorporate an integral guidewire tip which extends distally from the crooked retaining wire or the rotating hollow shaft, as the case may be. Alternatively, the device may be inserted in over the guidewire fashion, or in rapid exchange fashion (in which case the insertion catheter may be provided with a monorail tip).

Figure 7:
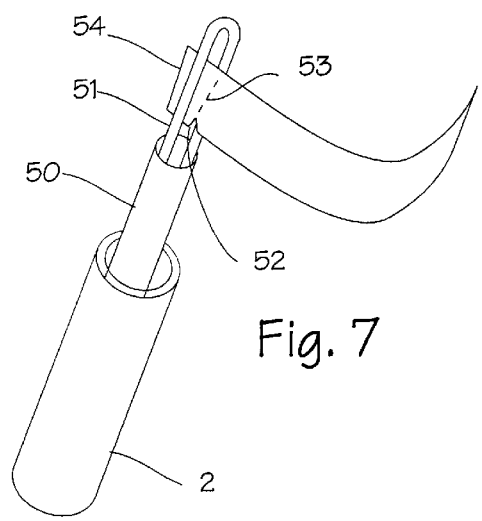
FIG. 7 shows an embodiment of the rotating stent deployment system with a tear-away tab release.

In FIG. 7 another embodiment of the rotating and retaining means is illustrated. The retaining means comprises a core 50 which includes a retaining wire 51 which is bonded at or near the inner edge 24 of the sheet 22. The starter notch 52 on the stent, located to correspond to the diameter of the core 43, creates a tear line 53 which separates the sheet into the major portion of the sheet 22 which will remain in the blood vessel after deployment, and a small tear-away tab 54 which will be torn from the major portion of the sheet in order to release the stent. During deployment the core 43 and the inner wire 44 are rotated to tighten the stent and facilitate longitudinal movement of the stent out of the distal end of the catheter and within the lumen of the blood vessel. When the stent is properly placed, the small tear-away tab can be retracted proximally using several gentle tugs, which strips off the major portion of the sheet 22 from the inner wire 44. The bonding can be achieved using cyanoacrylate adhesive (super glue) or any other suitable adhesive.

The various embodiments of the releasable retaining mechanism provide a dynamic rotational force that maintains the stent in a configuration in which longitudinal movement is facilitated. Rotation may be at such speed as to spin the stent into a smaller diameter, but this is not strictly necessary. It is sufficient that the stent be urged toward a more tightly wound condition, such that the outer layers may slide more freely over each other and past the inner surfaces of the catheter and blood vessel. The process is similar to that used to remove a roll of paper from a mailing tube, which often requires that the roll be twisted from an inside layer to loosen the roll within the mailing tube while the roll is pulled from the mailing tube. In this analogous situation, it is apparent that the roll of paper need not be spun so much that is actually takes on a smaller diameter, and that it is sufficient to remove the outwardly compressive force exerted by the inner rolls as they resiliently try to expand against the outer layers. We say that the roll of paper is rotated to urge the roll toward a smaller diameter configuration, realizing that the smaller diameter configuration need never be achieved. We also refer to the configuration achieved by rotation as the compacted configuration, realizing that this includes configurations in which inner layers are rotated into a tighter roll but outer layers may be tightened into a smaller diameter or may merely become loose compared to the inner layers, depending on the rotational speed applied. Such a compacted configuration is maintained at least in part by operation of the dynamic force applied by rotation, and expansion to the expanded configuration occurs at least in part by removal of the dynamic force.

Thus, while specific embodiments and applications of expandable stents have been disclosed and described in reference to the environment in which they were developed, they are merely illustrative of the principles of the inventions. Although described in reference to the treatment of blood vessels, the devices may be employed in any vessel of the body. It should be apparent to those skilled in the art that many more modifications besides those already described are possible without departing from the inventive concepts herein. For example, it is contemplated that new and better materials be discovered for use and intravascular stents. Similarly, it is possible to devise a number of releasable attachment means in addition to those illustrated. The inventive subject matter, therefore, is not to be restricted except in the spirit of the appended claims.

I claim:

1. A stent and stent delivery system for inserting a stent into a blood vessel and deploying the stent at a target site within the blood vessel, said stent delivery system comprising:

an insertion catheter of appropriate diameter, length and flexibility for insertion into the blood vessel and navigation within the blood vessel to a location at or near the target site;

a stent comprising a rolled sheet stent having a small diameter rolled configuration in which the stent fits within the lumen of the insertion catheter and a large diameter rolled configuration in which the stent fits within the blood vessel;

a longitudinally movable wire secured to the rolled sheet stent and extending to the proximal end of the insertion catheter;

a means for rotating the longitudinally movable wire, thereby causing rotation of the rolled sheet stent and facilitating longitudinal movement of the stent.

2. The stent delivery system of claim 1 wherein the movable wire is releasably connected to the rolled sheet stent.

3. The stent delivery system of claim 1 wherein the movable wire comprises a crook at the distal end of the movable wire and a portion of the rolled sheet stent passed through the crook and is retained to the wire by the crook.

4. The stent delivery system of claim 1 wherein the means for rotating the movable wire comprises a hand held motor.

5. The stent delivery system of claim 1 wherein the means for rotating the movable wire permits manual rotation of the movable wire.

6. The stent delivery system of claim 1 wherein the stent comprises a sheet of nitinol.

7. The stent delivery system of claim 1 wherein the stent comprises a sheet of perforated material.

8. A stent and stent delivery system for inserting a stent into a blood vessel and deploying the stent at a target site within the blood vessel, said stent delivery system comprising:

an insertion catheter of appropriate diameter, length and flexibility for insertion into the blood vessel and navigation within the blood vessel to a location at or near the target site;

stent comprising a rolled sheet stent having a small diameter rolled configuration in which the stent fits within the lumen of the insertion catheter and a large diameter rolled configuration in which the stent fits within the blood vessel;

a rotatable retaining means disposed within the insertion catheter and secured to the rolled sheet stent and operably connected to the rolled sheet stent to retain the stent inside the insertion catheter during insertion into the blood vessel and for rotating the stent to facilitate longitudinal movement of the stent during deployment.

9. The stent delivery system of claim 8 wherein the rotatable retaining means is releasably connected to the rolled sheet stent.

10. The stent delivery system of claim 8 wherein the rotatable retaining means comprises a rotatable and longitudinally movable wire comprises a crook at the distal end of the movable wire and a portion of the rolled sheet stent passes through the crook and is retained to the wire by the crook.

11. The stent delivery system of claim 8 further comprising a hand held motor for rotating the rotatable retaining means.

12. The stent delivery system of claim 5 wherein the stent comprises a sheet of nitinol.

13. The stent delivery system of claim 5 wherein stent comprises a sheet of perforated material.

14. A method of deploying a rolled sheet stent within a blood vessel, said method comprising:

provviding an insertion catheter with a lumen and inserting the rolled sheet stent into the lumen;

providing a means for rotating the rolled sheet stent within the lumen of the insertion catheter;

employing the means for rotating the rolled sheet stent to rotate the rolled sheet stent in a direction to urge the rolled sheet stent toward a compact configuration;

moving the rolled sheet stent longitudinally within the insertion catheter while rotating the rolled sheet stent in order to deploy the stent out of the insertion catheter and into the blood vessel;

slowing or ceasing the rotation of the rolled sheet stent to permit it to expand to an expanded configuration within the blood vessel.

15. The method of claim 14 further comprising the steps of:

providing a means for rotating the rolled sheet stent within the lumen of the insertion catheter, wherein the means for rotating is releasably attached to the rolled sheet stent;

releasing the rolled sheet stent from the means for rotating.

16. A method of deploying a rolled sheet stent within a blood vessel, said method comprising:

providing an insertion catheter with a lumen and inserting the rolled sheet stent into the lumen;

providing a means for rotating the rolled sheet stent within the lumen of the insertion catheter;

employing the means for rotating the rolled sheet stent to rotate the rolled sheet stent in a direction to urge the rolled sheet stent toward a compact configuration;

moving the rolled sheet stent longitudinally within the insertion catheter while rotating the rolled sheet stent in order to deploy the stent out of the insertion catheter and into the blood vessel;

slowing or ceasing the rotation of the rolled sheet stent to permit it to expand to an expanded configuration within the blood vessel;

wherein the means for rotating is releasably attached to the rolled sheet stent;

releasing the rolled sheet stent from the means for rotating;

engaging the rolled sheet stent with the means for rotating and resuming rotation of the rolled sheet stent;

moving the rolled sheet stent longitudinally within the blood vessel while rotating the rolled sheet stent in order to retrieve the stent from the blood vessel and pull it into the insertion catheter.

17. A method of temporarily deploying a rolled sheet stent within a blood vessel while performing other treatments on the blood vessel, said method comprising:

providing an insertion catheter with a lumen and inserting the rolled sheet stent into the lumen;

providing a means for rotating the rolled sheet stent within the lumen of the insertion catheter;

employing the means for rotating the rolled sheet stent to rotate the rolled sheet stent in a direction to urge the rolled sheet stent toward a compact configuration;

moving the rolled sheet stent longitudinally within the insertion catheter while rotating the rolled sheet stent in order to deploy the stent into the blood vessel;

slowing or ceasing the rotation of the rolled sheet stent to permit it to expand to an expanded configuration within the blood vessel;

performing other treatments on the blood vessel;

resuming rotation of the rolled sheet stent;

moving the rolled sheet stent longitudinally within the blood vessel while rotating the rolled sheet stent in order to retrieve the stent from the blood vessel and pull it into the insertion catheter.

18. A system for delivering a rolled sheet stent into a vessel of a body, wherein said rolled sheet stent comprises a sheet which may be expanded from a compacted configuration to an expanded configuration, said system comprising a catheter which houses the rolled sheet stent in the compacted configuration and, a means for applying a dynamic force to the stent to urge the stent toward its compacted configuration.

19. The stent of claim 18 wherein the means for applying dynamic force comprises a means for rotating the rolled sheet stent within the catheter.

* * * * *